(12) United States Patent
Ramos

(10) Patent No.: US 7,832,903 B2
(45) Date of Patent: Nov. 16, 2010

(54) ILLUMINATION SYSTEM FITTED WITH A THERAPEUTIC/PROPHYLACTIC FILTER FOR HEALTHY EYES, PSEUDOAPHAKIC EYES OR EYES SUFFERING NEURODEGENERATION

(75) Inventor: Celia Sanchez Ramos, Madrid (ES)

(73) Assignee: Universidad Complutense de Madrid, Madrid (ES)

( * ) Notice: Subject to any disclaimer, the term of this patent is extended or adjusted under 35 U.S.C. 154(b) by 84 days.

(21) Appl. No.: 11/936,464

(22) Filed: Nov. 7, 2007

(65) Prior Publication Data

US 2008/0180954 A1    Jul. 31, 2008

Related U.S. Application Data

(60) Provisional application No. 60/864,696, filed on Nov. 7, 2006.

(51) Int. Cl.
*F21V 9/00* (2006.01)
(52) U.S. Cl. .................. 362/293; 362/583; 362/260; 428/38; 428/426; 296/84.1; 296/97.1
(58) Field of Classification Search .............. 362/293, 362/260, 583; 296/84.1, 97.1; 252/586; 428/38, 426
See application file for complete search history.

(56) References Cited

U.S. PATENT DOCUMENTS

| | | | |
|---|---|---|---|
| 4,715,704 A | 12/1987 | Biber et al. | |
| 4,936,673 A | 6/1990 | Mauersberger | |
| 5,121,030 A | 6/1992 | Schott | |
| 5,690,421 A * | 11/1997 | Shea et al. | 362/293 |
| 5,774,202 A | 6/1998 | Abraham et al. | |
| 6,158,865 A | 12/2000 | Kreutzig | |
| 6,252,702 B1 | 6/2001 | Cook et al. | |
| 6,299,310 B1 | 10/2001 | Reis | |
| 6,315,411 B1 * | 11/2001 | Hatchiguian | 351/163 |

(Continued)

FOREIGN PATENT DOCUMENTS

DE            10259261         7/2004

(Continued)

OTHER PUBLICATIONS

Catherine A. McCarty, PHD. MPH et al., "Risk Factors for Age-Related Maculopathy The Visual Impairment Project", Arch Ophthalmol/vol. 119, Oct. 2001, pp. 1455-1462.

(Continued)

*Primary Examiner*—Sandra L O'Shea
*Assistant Examiner*—Jessica L McMillan
(74) *Attorney, Agent, or Firm*—Schiff Hardin LLP

(57) ABSTRACT

A device is provided for the treatment and prophylaxis of healthy eyes, pseudoaphakic eyes and/or eyes suffering macular and retinal degeneration that comprises a yellow filter applied to a conventional illumination system to protect them from short wavelengths of the visible spectrum under 500 nm and preferably in the range of 350 nm to 500 nm. This device the difficulties and risks of existing ways of protecting eyes undergoing cataract surgery and prevents or improves the degeneration of healthy eyes and those suffering neurodegeneration by the simple application of a protective filter to any lighting system. Embodiments of the invention comprise combining a conventional light source with a conventional yellow filter that absorbs wavelengths of light shorter than 500 nm so that the filter completely covers the illumination source.

32 Claims, 1 Drawing Sheet

U.S. PATENT DOCUMENTS

| | | |
|---|---|---|
| 6,893,127 B2 | 5/2005 | Reichow et al. |
| 2002/0113941 A1 | 8/2002 | Bees |
| 2004/0075810 A1 | 4/2004 | Duha et al. |
| 2004/0252507 A1* | 12/2004 | New et al. .................. 362/260 |
| 2006/0141466 A1* | 6/2006 | Pinet et al. .................... 435/6 |
| 2006/0195278 A1 | 8/2006 | Lianza |

FOREIGN PATENT DOCUMENTS

| | | |
|---|---|---|
| ES | 1046793 U | 2/2001 |
| FR | 2811089 | 1/2002 |
| GB | 88 08 871.5 | 10/1988 |
| GB | 2 368 446 | 5/2002 |
| IT | 1147092 | 11/1986 |
| JP | 58049514 | 3/1983 |
| JP | 59126935 | 7/1984 |
| JP | 61087106 | 5/1986 |
| JP | 5193397 | 8/1993 |
| JP | 10020347 | 1/1998 |
| JP | 10315763 | 12/1998 |
| JP | 2000349541 | 12/2000 |
| JP | 2000349542 | 12/2000 |
| KR | 9205420 | 7/1992 |
| WO | WO 99/27397 | 6/1999 |
| WO | WO 2005/025575 | 3/2005 |

OTHER PUBLICATIONS

Ellen E. Freeman, MSc et al., "Is There an Association Between Cataract Surgery and Age-Related Macular Degeneration? Data From Three Population-based Studies", 2003 by Elsevier Inc., pp. 849-856.

J. J. Wang et al., "Cataract and age-related maculopathy: the Blue Mountains Eye Study", Ophthalmic Epidemiology-1999, vol. 6, No. 4, pp. 317-326.

Ronald Klein, MD, MPH et al., "The Association of Cataract and Cataract Surgery With the Long-term Incidence of Age-Related Maculopathy", Arch Ophthalmol/ col. 120, Nov. 2002, pp. 1551-1558.

* cited by examiner

ILLUMINATION SYSTEM FITTED WITH A THERAPEUTIC/PROPHYLACTIC FILTER FOR HEALTHY EYES, PSEUDOAPHAKIC EYES OR EYES SUFFERING NEURODEGENERATION

CROSS REFERENCE TO RELATED APPLICATIONS

The present application claims the benefit of U.S. Provisional Application No. 60/864,696, filed Nov. 7, 2006, entitled, "Illumination System Fitted with a Therapeutic/Prophylactic Filter for Healthy Eyes, Pseudoaphakic Eyes or Eyes Suffering Neurodegeneration", herein incorporated by reference.

BACKGROUND

The invention is intended for the opthalmology sector of the market, within the area of optical applications of a therapeutic and/or prophylactic nature.

The object of this invention is a device for the protection of healthy eyes, pseudoaphakic eyes (eyes that have undergone cataract surgery) and/or eyes with macular and retinal degeneration, produced by applying a yellow pigment, or filter, to an illumination system. The device protects the eye from the short wavelengths of the visible spectrum (<500 nm).

Referring to FIG. 1, visual perception is the result of the response to visible radiation in the wavelength range 380-760 nm. In the environment, solar radiation is the main risk factor for vision. The sun emits ultraviolet (UV) rays and infra-red (IR) radiation, which are mainly absorbed by the atmosphere. When the solar radiation transmitted through the atmosphere reaches the Earth's surface, it consists of UV-B rays (230-300 nm), UV or UV-A rays (300-380 nm), visible light rays (380-760 nm) and IR rays (760-1400 nm). Healthy human eyes freely transmit IR rays and those of most of the visible spectrum to the retina, but the cornea and crystalline lens prevent the most reactive wavelengths of the light spectrum (UV-B rays, UV-A rays, and the violet/blue portion of the spectrum) from reaching the retina.

The human crystalline lens changes its transmission properties as it ages by intensifying its yellowish color, thus increasing its capacity to filter out UV and violet/blue light rays. Hence, in persons older than 65 years, ultraviolet light (<400 nm) is not transmitted and the transmission of violet/blue light (400-500 nm) is markedly reduced.

The retina is capable of protecting itself from short wavelengths of light in two ways: through its uneven distribution of photoreceptors, such that there are no photoreceptors sensitive to violet/blue light in the macular depression; and through the actions of yellow pigments in this zone, which also exert a protective effect.

These natural protection systems against the shorter wavelengths of light in the human eye—the crystalline lens and structures of the retina—can be seriously affected by certain diseases and/or surgical procedures:

Cataracts, whose surgical treatment involves the removal of the crystalline lens;

Additionally, it is common to find a pathological ageing process that causes degradation of the retinal structures producing age-related macular degeneration (AMD).

Both cataracts and AMD can coexist in persons older than 65 years. In this population of elderly subjects, cataracts are the main cause of vision loss, and AMD is the main cause of blindness. In addition, an increase in both these diseases due, among other factors, to our increased life expectancy, can be expected. This translates into a great interest in these diseases and their treatment options in the research field and optics industry.

Several epidemiological studies have evaluated the relationship between cataract surgery and AMD. For example, Klein (Klein R, Klein B E, Wong T Y, Tomany S C, Cruickshanks K J. The association of cataract and cataract surgery with the long-term incidence of age-related maculopathy. *Arch Opthalmol* 120:1551-1558.2002) and Freeman (Freeman E, Muñoz B, West S K, Tielsch J M, Schein O D. Is there an association between cataract surgery and age-related macular degeneration? *Am J Opthalmolm* 135(6): 849-856.2003) claim there is a higher risk of developing symptoms of AMD in persons who have undergone cataract surgery.

However, in earlier investigations by Wang (Wang J J, Mitchell P, Cumming R G, Lim R. Cataract and age-related maculopathy: the Blue Mountains Eye Study. *Ophthalmic Epidemiol* 6: 317-326.1999) and McCarty (McCarty C A, Mukesh B N, Fu C L, Mitchell P, Wang J J, Taylor H R. Risks factors for age-related maculopathy: the Visual Impairment Project. *Arch Opthalmol* 119:1455-1462, 2001) this hypothesis was rejected, possibly because of the less developed technology used for their diagnostic measurements. Techniques such as optical coherence tomography that allow the accurate, rapid and non-invasive follow up of retinal neurodegeneration processes have only recently been introduced. These techniques are essential for establishing the determining effect of the natural pigments that absorb harmful radiations.

Several techniques have also been developed to protect eyes subjected to cataract surgery from short wavelengths of light:

There are several types of filters containing a yellow pigment on the market, yet there is no optimal procedure and/or device to apply these filters to the human eye as a preventive and/or therapeutic measure to replace and/or improve the eye's natural protection Since the mid-1990s, eyes undergoing cataract extraction have been implanted with intraocular lenses containing a yellow pigment to act as a filter. This option requires surgical intervention with all its risks and difficulties. There is also a large population of subjects who have been implanted with a transparent lens to replace the natural lens during cataract surgery who are therefore devoid of the necessary protection. In these patients, the artificial crystalline lens, lacking a yellow pigment, needs to be complemented with a system to support the yellow pigment.

Several patents related to the state of this technique have been developed although they differ considerably from the object of the present invention, as described by the following references, all herein incorporated by reference:

An absorption filter for colour exposure systems (U.S. Pat. No. 5,121,030) that, through the use of dyes, improves visibility in conditions of intense luminosity.

A color-enhancing filter and method of use to improve the vision of the human eye (U.S. Pat. No. 6,158,865). This invention includes a filter that improves vision in all conditions of light including extreme ambient light and low illumination levels and includes an adapting ring for the filter.

Special optical filters for certain activities and optical accessories that use these filters (U.S. Pat. No. 6,893,127) to improve the visualization of objects, for example in sports activities.

An optical filter and device, filter that absorbs heat rays, optic fiber and spectacles equipped with this optic filter (International Patent Publication No. WO 99 27397). The filter is composed of a synthetic resin capable of protecting from wavelengths of light in the infrared region.

A method for designing colour filters that improve or modify the colour vision of the human eye and colour filtrating media designed by the method (U.S. Patent Publication No. 2004/075810).

A system and method for applying correction factors related to the environmental conditions (U.S. Patent Publication No. 2006/195278) based on a colour detector programmed by software and/or hardware to counteract environmental conditions.

A protection solution for the treatment of eyes (International Patent Publication No. WO 2005 025575), composed mainly of a viscoelastic fluid or rinse containing substances that, at least in part, filter specific frequencies of light radiation.

A protection and correction device for the human eye that includes a set of filters to protect against electromagnetic radiation and/or corrects visual defects such as myopia or lack of colour vision (German Patent Document No. DE 1 0259 261)

An optical vision system that includes a device for partially reducing the illumination intensity (U.S. Patent Publication No. 2002/113941), as, for example, a surgical microscope, that includes a spectral filter adapted to reduce, without eliminating, the intensity of light emitted from a light source in a specific region of the object (which could be the human eye).

A system for the detection and control of light intensity for ocular and projecting microscope lamps (U.S. Pat. No. 6,299,310, based on U.S. Pat. No. 4,715,704) that allows work at a high level of illumination of the eye under examination and also avoids damage to the eye being examined.

A diffusion plate combined with a microscope lamp (German Patent Document No. 8 808 871) that controls the light emitted by the lamp.

An LED system (light emitting diode) for eye examinations (Italian Patent No. 1 147 092) that may incorporate filters.

A solid phometer—apparatus for detecting eye and optic nerve defects that includes the use of neutral intensity filters.

These devices differ from the present invention mainly in their purpose and utility since none has been designed to protect healthy eyes, eyes subjected to cataract surgery or eyes suffering neurodegeneration from short wavelengths of light.

Moreover, most of these prior art documents do not refer to the application of a filter to a conventional lamp used to illuminate a work, recreation, or home area; rather they are designed to be used in other contexts (e.g., special-purpose lighting systems, lenses, solutions, etc.)

SUMMARY

The objective of the invention, in the case of pseudoaphakic subjects is to functionally compensate for the removal of protective pigments (along with the natural lens during surgery) and in the case of healthy eyes or eyes suffering neurodegeneration processes, is to potentiate the prophylactic effect of the absorption of violet/blue and ultra violet light by applying a filter to the conventional lighting system(s) normally used to illuminate areas where people are present, such as rooms, desks, indoor work or play areas, and outdoor work or play areas. As mentioned, it is very common that retinal neurodegeneration and cataracts coexist in elderly persons.

Accordingly, a therapeutic and prophylactic illumination device is provided for the protection of pseudoaphakic eyes, comprising: a conventional area illumination device that outputs light in the visual spectrum of light frequencies to cover a lighted area; a yellow filter that absorbs short wavelengths of light below 500 nm, that covers all of the illumination device output; and a mount that holds the yellow filter in place relative to the illumination device in order to maintain the coverage. In an embodiment, the yellow filter absorbs light within the wavelength range of 350 to 500 nm. The illumination device may be a fluorescent, halogen, or incandescent light. The mount can be a support or a frame, and the lighted area can be a room, a desk, or an indoor or outdoor work or play area.

DESCRIPTION OF THE DRAWINGS

The invention is explained with reference to an embodiment illustrated in the drawings and described in detail below.

DESCRIPTION OF THE EMBODIMENTS OF THE INVENTION

Figure 1:
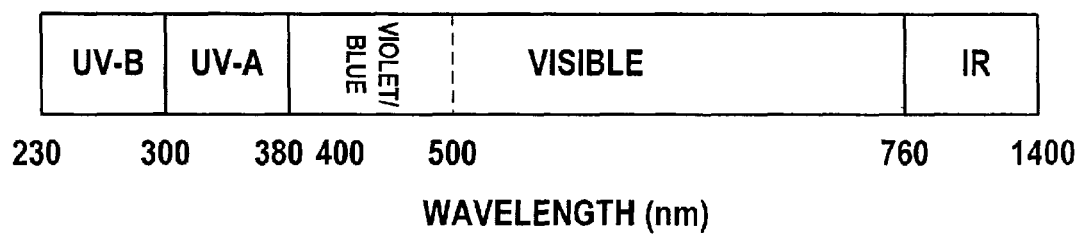
FIG. 1 is a chart illustrating the various frequencies of electromagnetic radiation.
Figure 2:
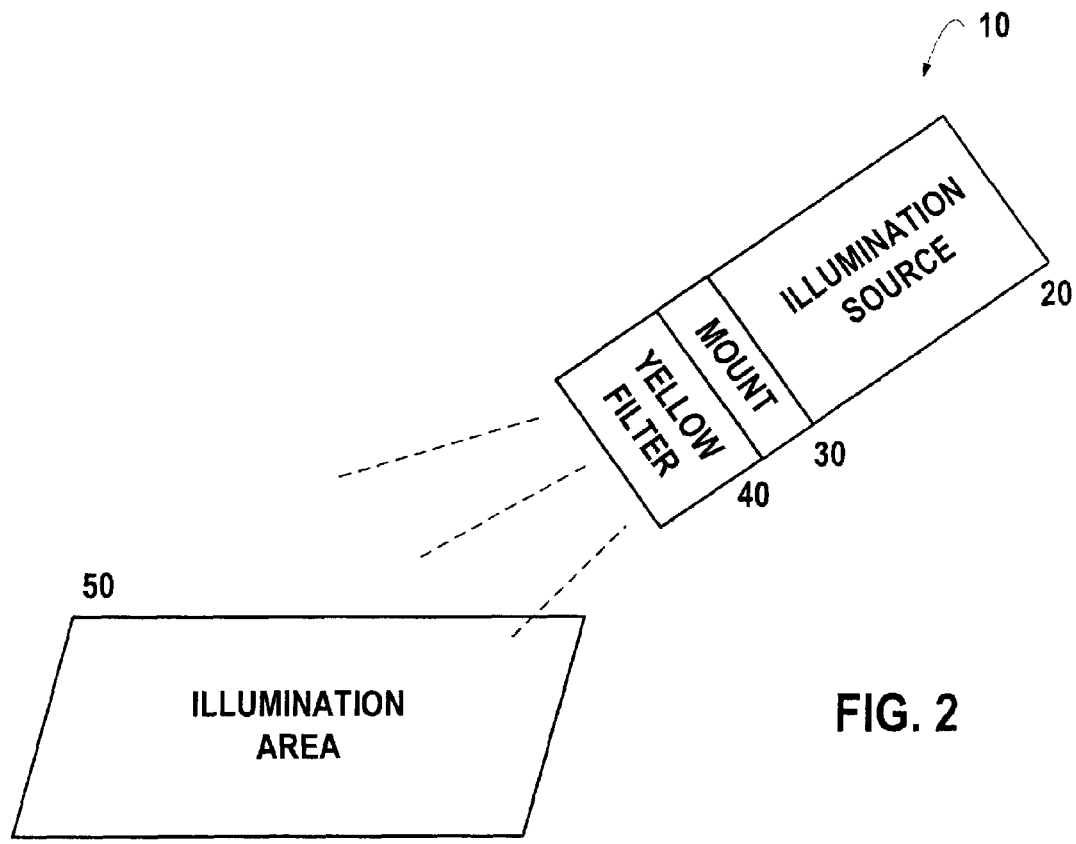
FIG. 2 is a block diagram illustrating the primary components.

According to an embodiment of the invention, and referring to FIG. 2, an illumination device 10 is provided that protects healthy or diseased eyes from neurodegeneration by absorbing harmful light rays by way of a yellow filter that absorbs short wavelengths of light between 350 and 500 nm, which is applied to a conventional lighting system.

Referring to FIG. 2, the device 10 includes the three elements: 1) a normal illumination source 20 such as an incandescent, fluorescent or halogen lamp; 2) a frame, support, or mount 30 to apply a yellow filter 40 to the illumination source's 20 lamp; and 3) the yellow filter 40, among those available on the market, compatible with the illumination system that absorbs short wavelengths of light in the range 350 to 500 nm across all of the light emitting/illumination area 50.

Preparation According to Embodiments of the Invention

There are several ways of manufacturing embodiments of the invention depending on the type of illumination system 10 used. The illustrations below are provided by way of example but are in no way restrictive, there being many different ways of elaborating the device.

In one embodiment, a yellow filter 40 is selected from those commercially available, for instance, in the form of a screen or dye that is compatible with the illumination source 20. A support material 30 is then selected from those available on the market to apply the filter 40 to the illumination source 20 according to the manufacturers instructions or, for example, according to the Spanish patent documents EO 1 830 250 (filter support junction for illumination systems) or ES 1 046 793 (filter support structure for illumination systems), both herein incorporated by reference. The yellow filter 40 is mounted on the support 30 such that it covers all the light-emitting area of the lighting source 20.

In summary, combining a yellow filter 40 with an illumination source 20 compensates for the lack of natural protection suffered by patients operated on for cataracts implanted with a transparent intraocular lens and helps improve and increase the natural protection of eyes undergoing neurodegeneration as well as prevent neurodegeneration processes in healthy eyes. This simple set up avoids the problems related to the technical options available on the market that require surgery for the implant of an intraocular lens.

For the purposes of promoting an understanding of the principles of the invention, reference has been made to the preferred embodiments illustrated in the drawings, and specific language has been used to describe these embodiments. However, no limitation of the scope of the invention is intended by this specific language, and the invention should be construed to encompass all embodiments that would normally occur to one of ordinary skill in the art.

The present invention may be described in terms of functional block components and various processing steps. Such functional blocks may be realized by any number of hardware components configured to perform the specified functions. The particular implementations shown and described herein are illustrative examples of the invention and are not intended to otherwise limit the scope of the invention in any way. For the sake of brevity, conventional electronics, control systems, software development and other functional aspects of the systems (and components of the individual operating components of the systems) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device. Moreover, no item or component is essential to the practice of the invention unless the element is specifically described as "essential" or "critical". The word mechanism is intended to be used generally and is not limited solely to mechanical embodiments. Numerous modifications and adaptations will be readily apparent to those skilled in this art without departing from the spirit and scope of the present invention.

What is claimed is:

1. A therapeutic and prophylactic illumination device for protection of pseudoaphakic eyes, comprising:
    a conventional area illumination device having an output that outputs light in the visual spectrum of light frequencies to cover a lighted area;
    a yellow filter that absorbs wavelengths of light within the wavelength range of 350 to 500 nm, that covers all of the output of the illumination device; and
    a mount that holds the yellow filter in place relative to the illumination device in order to filter substantially all light output by the illumination device to thereby provide the therapeutic and prophylactic illumination device for protection of pseudoaphakic eyes.

2. A therapeutic and prophylactic illumination device according to claim 1, wherein the illumination device is a fluorescent light.

3. A therapeutic and prophylactic illumination device according to claim 1, wherein the illumination device is a halogen light.

4. A therapeutic and prophylactic illumination device according to claim 1, wherein the illumination device is an incandescent light.

5. A therapeutic and prophylactic illumination device according to claim 1, wherein the mount is a support or a frame.

6. A therapeutic and prophylactic illumination device according to claim 1, wherein the lighted area is a room.

7. A therapeutic and prophylactic illumination device according to claim 1, wherein the lighted area is a desk.

8. A therapeutic and prophylactic illumination device according to claim 1, wherein the lighted area is an outdoor work area.

9. A method for protecting healthy eyes, said method comprising the steps of:
    illuminating an area to be lit using an illumination device including a conventional area illumination device that outputs light in the visual spectrum of light frequencies over the area to be lit;
    filtering light output by the illuminating device using a yellow filter configured to absorb relative short wavelengths of light within the wavelength range of 350 to 500 nm, said filtering step filtering substantially all of the light output by the illumination device; and
    holding the yellow filter in place relative to the illumination device in order to maintain coverage by the yellow filter of substantially all light output by the illuminating device to protect healthy eyes from the effects of light in the wavelength range of 350 to 500 nm.

10. A method as claimed in claim 9, wherein said step of illuminating is performed by a fluorescent light.

11. A method as claimed in claim 9, wherein said step of illuminating is performed by a halogen light.

12. A method as claimed in claim 9, wherein said step of illuminating is performed by an incandescent light.

13. A method as claimed in claim 9, wherein said step of holding is performed by a support or a frame.

14. A method as claimed in claim 9, wherein said step of illuminating lights a room.

15. A method as claimed in claim 9, wherein said step of illuminating lights a desk.

16. A method as claimed in claim 9, wherein said step of illuminating lights an outdoor work area.

17. A method for protecting pseudoaphakic eyes, said method comprising the steps of:
    illuminating an area to be lit using a illumination device including a conventional area illumination device that outputs light in the visual spectrum of light frequencies toward the area to be lit;
    filtering light output by the illumination device using a yellow filter configured to absorb a relative short wavelengths of light within a wavelength range of 350 to 500 nm, the yellow filter being positioned to cover substantially all light output from the illumination device; and
    holding the yellow filter in place relative to the illumination device using a mount to provide illumination that protects pseudoaphakic eyes.

18. A method according to claim 17, wherein said step of illuminating uses a fluorescent light.

19. A method according to claim 17, wherein said step of illuminating uses a halogen light.

20. A method according to claim 17, wherein said step of illuminating uses an incandescent light.

21. A method according to claim 17, wherein said step of holding uses a support or a frame.

22. A method according to claim 17, wherein the area to be lit is a room.

23. A method according to claim 17, wherein the area to be lit is a desk.

24. A method according to claim 17, wherein the area to be lit is an outdoor work area.

25. A method for protecting eyes suffering neurodegeneration, said method comprising the steps of:

illuminating an area to be lit using an illumination device including a conventional area illumination device that outputs light in the visual spectrum of light frequencies toward the area to be lit;

filtering light output by the illuminating device using a yellow filter configured to absorb a relative short wavelengths of light within the wavelength range of 350 to 500 nm, the yellow filter being positioned to covers substantially all light output from the illumination device; and holding the yellow filter using a mount that holds the yellow filter in place relative to the illumination device in order to maintain the coverage to protect eyes suffering neurodegeneration.

26. A method according to claim 25, wherein said step of illuminating uses a fluorescent light.

27. A method according to claim 25, wherein said step of illuminating uses a halogen light.

28. A method according to claim 25, wherein said step of illuminating uses an incandescent light.

29. A method according to claim 25, wherein said step of holding uses a support or a frame.

30. A method according to claim 25, wherein the area to be lit is a room.

31. A method according to claim 25, wherein the area to be lit is a desk.

32. A method according to claim 25, wherein the area to be lit is an outdoor work area.

* * * * *